(12) United States Patent  
Takata et al.

(10) Patent No.: US 11,963,719 B2
(45) Date of Patent: Apr. 23, 2024

(54) LIGHT IRRADIATING MEDICAL DEVICE

(71) Applicant: KANEKA CORPORATION, Osaka (JP)

(72) Inventors: Hironori Takata, Settsu (JP); Kohei Fukaya, Settsu (JP)

(73) Assignee: KANEKA CORPORATION, Osaka (JP)

(*) Notice: Subject to any disclaimer, the term of this patent is extended or adjusted under 35 U.S.C. 154(b) by 525 days.

(21) Appl. No.: 17/276,036

(22) PCT Filed: Aug. 30, 2019

(86) PCT No.: PCT/JP2019/034155
§ 371 (c)(1),
(2) Date: Mar. 12, 2021

(87) PCT Pub. No.: WO2020/071023
PCT Pub. Date: Apr. 9, 2020

(65) Prior Publication Data
US 2022/0047331 A1 Feb. 17, 2022

(30) Foreign Application Priority Data

Oct. 1, 2018 (JP) .................................. 2018-186895

(51) Int. Cl.
*A61B 18/24* (2006.01)
*A61B 90/00* (2016.01)
*A61B 18/00* (2006.01)

(52) U.S. Cl.
CPC .............. *A61B 18/24* (2013.01); *A61B 90/39* (2016.02); *A61B 2018/0022* (2013.01); *A61B 2090/3966* (2016.02)

(58) Field of Classification Search
CPC . A61B 18/24; A61B 90/39; A61B 2090/3966; A61B 2018/0022
(Continued)

(56) References Cited

U.S. PATENT DOCUMENTS 5,879,306 A 3/1999 Fontenot et al.
5,989,243 A * 11/1999 Goldenberg ......... A61B 18/245
606/7
(Continued)

FOREIGN PATENT DOCUMENTS

JP 2-88051 A 3/1990
JP 10-108827 A 4/1998
(Continued)

OTHER PUBLICATIONS

International Search Report for PCT/JP2019/034155 dated Nov. 19, 2019.

*Primary Examiner* — Aaron F Roane
(74) *Attorney, Agent, or Firm* — Birch, Stewart, Kolasch & Birch, LLP

(57) ABSTRACT

A light irradiating medical device 1 includes a catheter shaft 2 extending in a longitudinal direction; a balloon 5 disposed at a distal portion of the catheter shaft 2; a light guiding tool 10 disposed in a lumen of the catheter shaft 2 and movable in the longitudinal direction, the light guiding tool 10 including an optical fiber 11 extending in the longitudinal direction and a tubular member 15 covering the optical fiber 11 and having light transparency, the optical fiber 11 including a core 12, a cladding 13 and a cladding absent portion 14 disposed at a part of a distal portion of the core 12; a first radiopaque marker 21 disposed at the distal portion of the catheter shaft 2; and a second radiopaque marker 22 disposed at the tubular member 15 at a position distal to a distal end 12a of the core 12.

14 Claims, 5 Drawing Sheets

(58) Field of Classification Search
USPC .......................................................... 606/15
See application file for complete search history.

(56) References Cited

U.S. PATENT DOCUMENTS

| | | | |
|---|---|---|---|
| 7,532,920 B1 * | 5/2009 | Ainsworth | A61B 5/02007 |
| | | | 600/478 |
| 2005/0065504 A1 | 3/2005 | Melsky et al. | |
| 2015/0216620 A1 | 8/2015 | Davies et al. | |
| 2017/0027458 A1 * | 2/2017 | Glover | A61B 5/6851 |

FOREIGN PATENT DOCUMENTS

| | | |
|---|---|---|
| JP | 11-169463 A | 6/1999 |
| JP | 2001-129094 A | 5/2001 |
| JP | 2012-507342 A | 3/2012 |
| JP | 2015-518752 A | 7/2015 |
| WO | WO 2007/007560 A1 | 1/2007 |
| WO | WO 2010/050965 A1 | 5/2010 |

* cited by examiner

[Fig. 1]
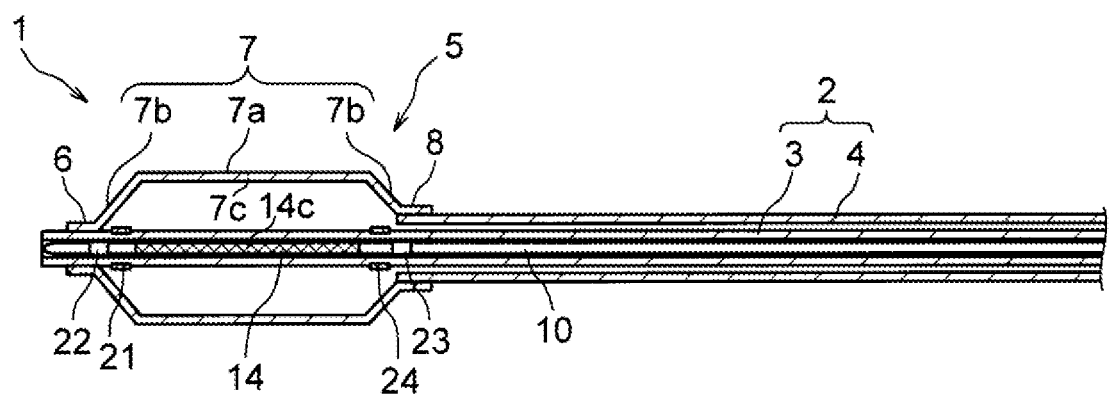
[Fig. 2]
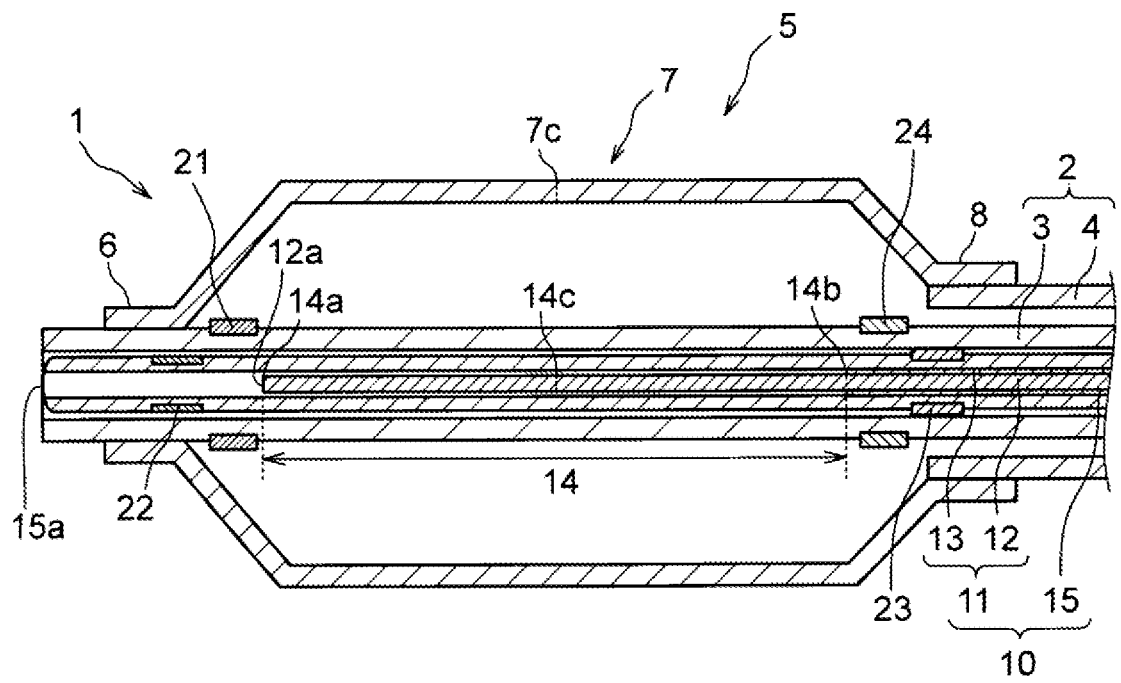

[Fig. 3]
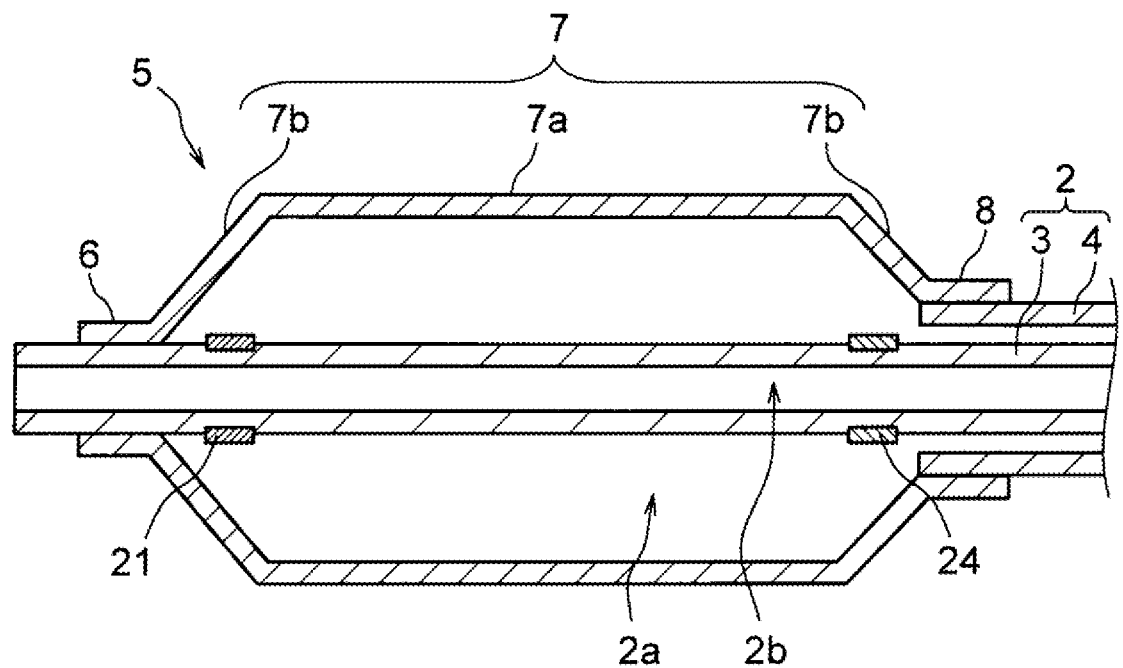
[Fig. 4]
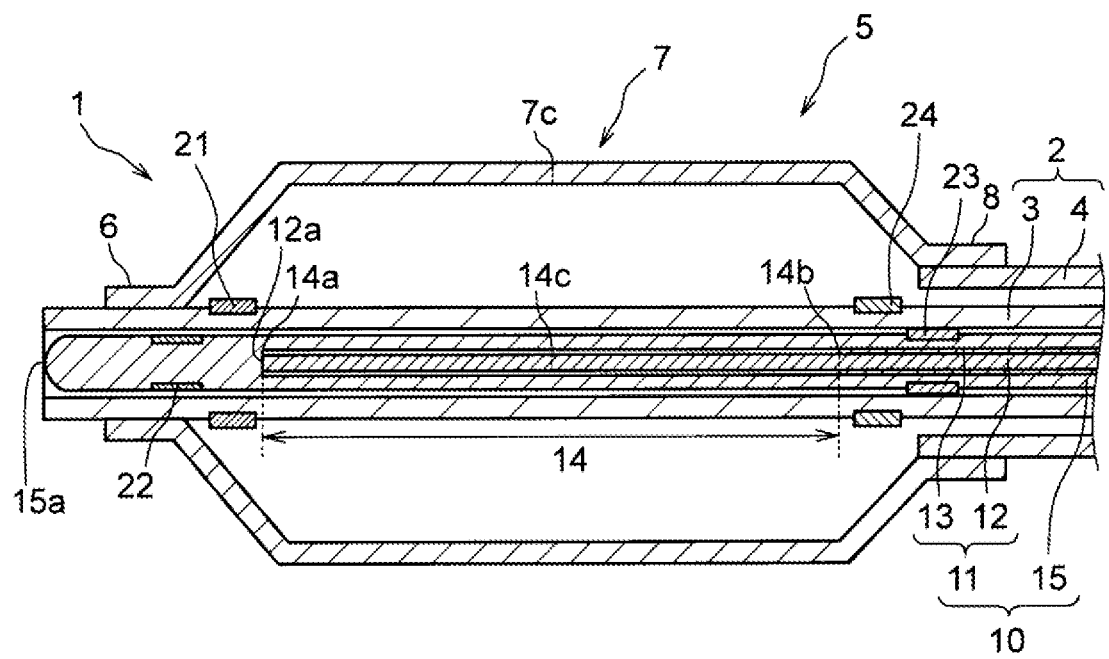

[Fig. 5]
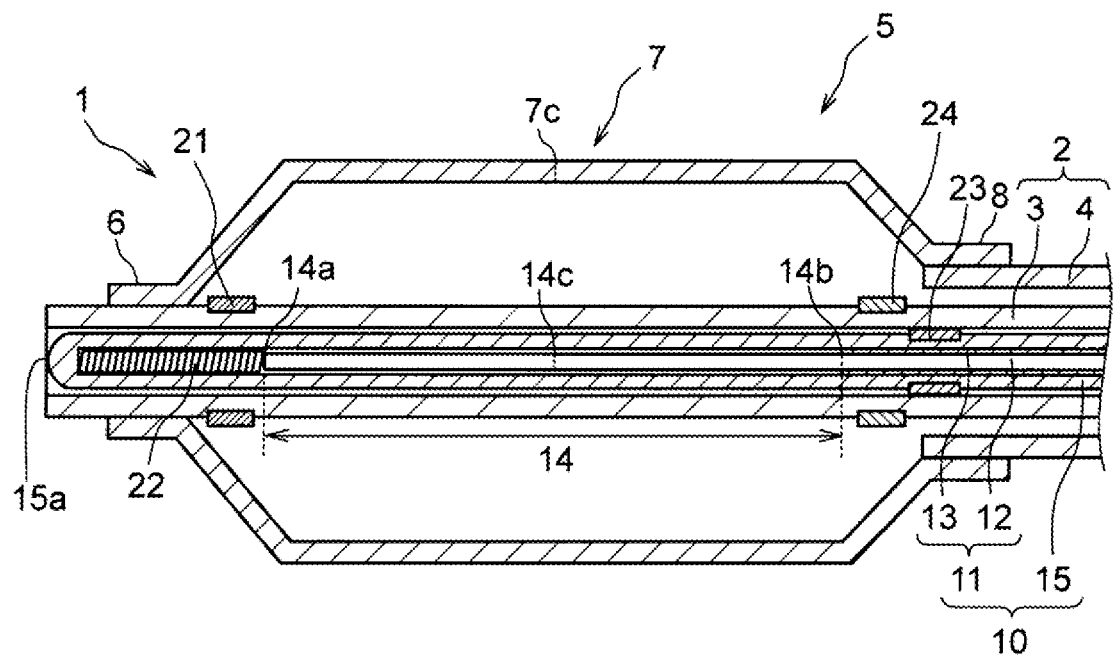
[Fig. 6]
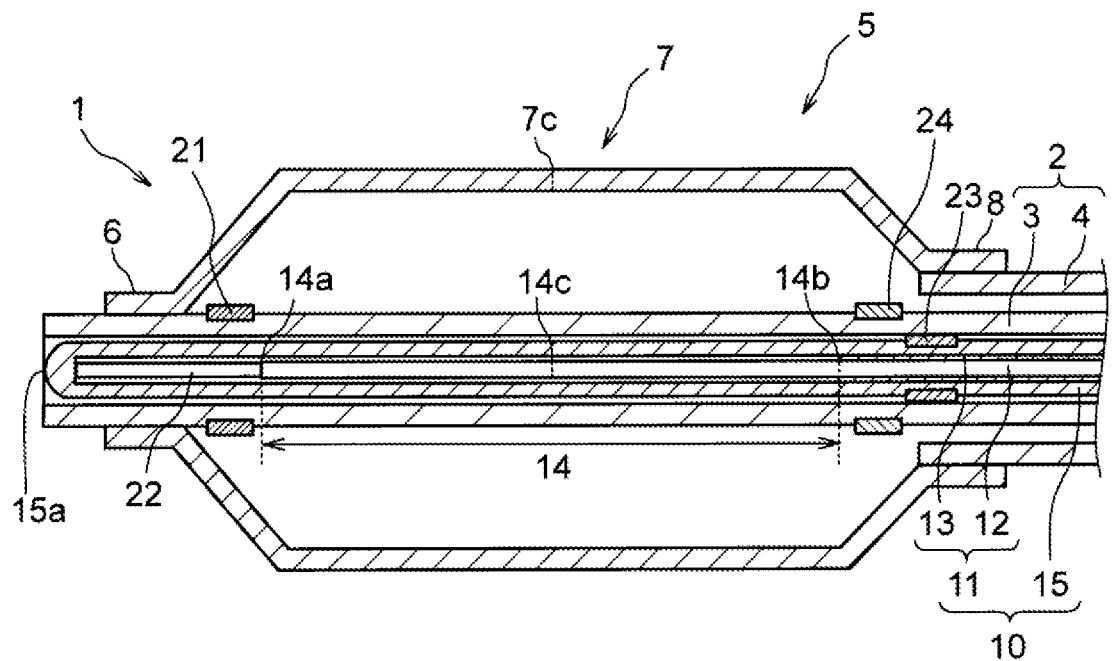

[Fig. 7]
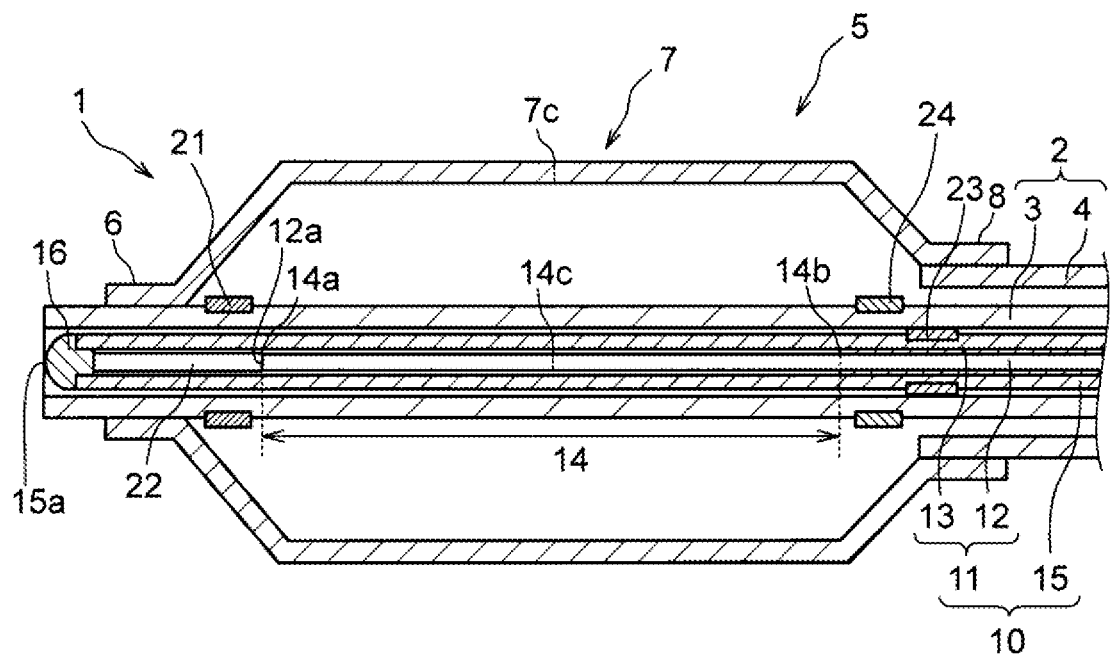
[Fig. 8]
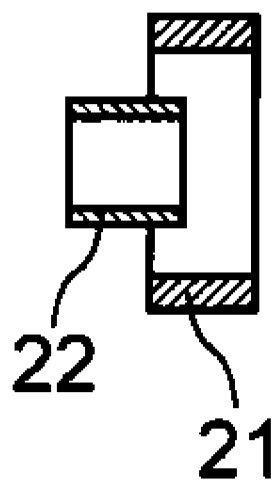

[Fig. 9]
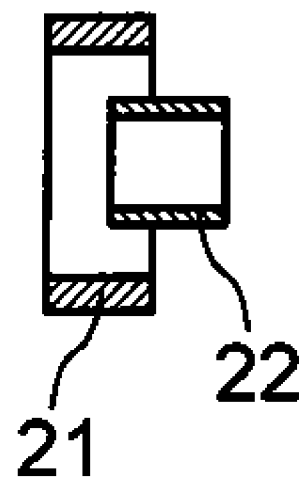

LIGHT IRRADIATING MEDICAL DEVICE

TECHNICAL FIELD

The present invention relates to a light irradiating medical device configured to irradiate a tissue such as a cancer cell with light in an endolumen such as a blood vessel or a gastrointestinal tract.

BACKGROUND ART

Photodynamic therapy (PDT) involves administering a photosensitizer into a body by means of intravenous injection or intraperitoneal administration, accumulating the photosensitizer in a target tissue such as a cancer cell, and irradiating with light having a specific wavelength to excite the photosensitizer. The excited photosensitizer returns into a ground state to cause energy conversion and generation of active oxygen species. The active oxygen species attack the target tissue to remove the target tissue. Furthermore, ablation with use of laser light (tissue cauterization) involves irradiating the target tissue with laser light to cauterize the target tissue.

PDT and optical ablation are executed with use of a light irradiating medical device including an optical fiber disposed in a catheter tube and configured to irradiate a target tissue with light. For example, Patent Document 1 discloses disposing, in a first bore in a catheter tube, an optical fiber configured to transmit laser energy from a proximal end portion of the catheter tube to a distant end portion of the catheter tube. The distant end portion and the vicinity of the catheter tube are surrounded with a catheter balloon, and the catheter tube has a radiopaque mark surrounding a distal end portion of the catheter tube. The catheter tube is positioned in a body with use of a guide wire, and the guide wire is then extracted from the catheter tube and the optical fiber is inserted through the catheter tube.

Patent Document 2 discloses a guide catheter for a laser fiber, including a shaft that allows the laser fiber to be inserted to the shaft. The shaft accommodates a stopper positioning the laser fiber in a longitudinal direction. The stopper divides the inside of the shaft into a lumen for the laser fiber and a lumen for a guide wire.

Patent Document 3 discloses an optical radiation fiber positioned in a catheter provided with a balloon and supporting a radiopaque marker.

RELATED ART DOCUMENTS

Patent Documents

Patent Document 1: JP-A-1102-88051
Patent Document 2: JP-A-2001-129094
Patent Document 3: JP-A-H10-108827

SUMMARY OF THE INVENTION

Technical Problem

In the catheter described in Patent Document 1, the optical fiber is not provided with any marker and cannot be positionally checked during X-ray fluoroscopy. Also in the catheter described in Patent Document 2, the optical fiber is not provided with any marker and cannot be positionally specified until contacting the stopper. Patent Document 3 does not describe any specific aspect on attaching the marker to the optical fiber, and the optical fiber may be deformed or damaged depending on an attached position or an attaching method. There has been expected improvement in a method of positionally specifying a light emitting area of an optical fiber in the longitudinal direction of a catheter. In view of this, it is an object of the present invention to provide a light irradiating medical device that enables protection of an optical fiber as well as facilitated positional specification of a light emitting area.

Solutions to the Problems

The gist of a light irradiating medical device according to the present invention that can overcome the above problems is as follows. A light irradiating medical device includes a catheter shaft extending in a longitudinal direction; a balloon disposed at a distal portion of the catheter shaft; and a light guiding tool disposed in a lumen of the catheter shaft and movable in the longitudinal direction, the light guiding tool including an optical fiber extending in the longitudinal direction and a tubular member covering the optical fiber and having light transparency, the optical fiber including a core and a cladding covering an outside of the core, and the optical fiber including a cladding absent portion disposed at a part of a distal portion of the core, the light irradiating medical device further includes a first radiopaque marker disposed at the distal portion of the catheter shaft; and a second radiopaque marker disposed at the tubular member at a position distal to a distal end of the core.

According to the light irradiating medical device configured as described above, the first radiopaque marker can specify a position of the catheter shaft during X-ray fluoroscopy, so that the balloon disposed at the catheter shaft can positionally match an irradiation target tissue. Since the balloon is disposed at catheter shaft, the balloon being expanded is in contact with an irradiation target tissue so that the catheter shaft can be fixed in the body. Furthermore, the second radiopaque marker is disposed distal to the distal end of the core, to prevent deformation and damage of the core due to stress generated upon attachment of the second radiopaque marker to the tubular member as well as to facilitate positional specification of the cladding absent portion serving as the light emitting area of the optical fiber during X-ray fluoroscopy. Checking a positional relation between the first radiopaque marker and the second radiopaque marker facilitates positioning the light emitting area at the irradiation target tissue and also reduces a work burden of an operator.

Preferably, the second radiopaque marker has a ring shape and is attached to an outside of the tubular member, and the tubular member has a portion with the second radiopaque marker and the portion has an outer diameter smaller than an outer diameter of a portion of the tubular member without the second radiopaque marker. In this case, the second radiopaque marker can be attached to be buried in an outer surface of the tubular member, to suppress increase in outer diameter of the tubular member at the portion with the second radiopaque marker. Furthermore, this configuration enables treatment of a deep tissue or an endoluminal tissue having a small inner diameter, which has not been reached so far.

Preferably, the second radiopaque marker is disposed in a lumen of the tubular member at a position distal to the distal end of the core. The light guiding tool can be decreased in diameter at the position distal to the distal end of the core in this configuration.

Preferably, the first radiopaque marker has a ring shape and is attached to an outside of the catheter shaft, and the second radiopaque marker has a length in the longitudinal direction larger than a length in the longitudinal direction of the first radiopaque marker. The second radiopaque marker is not completely hidden behind the first radiopaque marker even in the case where the two markers are overlapped with each other. This configuration facilitates positional specification of the light emitting area of the optical fiber.

Preferably, the second radiopaque marker has a coil shape. The second radiopaque marker having the coil shape in this manner causes the light guiding tool to be more deformable at a position distal to the distal end of the core so as to follow a shape of the endolumen.

Preferably, the second radiopaque marker has a bar shape. This shape simplifies a step of forming the second radiopaque marker.

Preferably, the light irradiating medical device further includes a third radiopaque marker disposed at the tubular member at a position proximal to a proximal end of the cladding absent portion. The radiopaque markers are thus disposed at respective ends of the cladding absent portion serving as the light emitting area in the longitudinal direction of the tubular member, to further facilitate positional specification of the light emitting area during X-ray fluoroscopy.

Preferably, the light irradiating medical device further includes a fourth radiopaque marker disposed at the catheter shaft at a position proximal to the first radiopaque marker. This configuration further facilitates positional specification of the catheter shaft in the longitudinal direction during X-ray fluoroscopy.

Preferably, the balloon includes a distal fixed portion fixed to the catheter shaft, an inflated portion not fixed to the catheter shaft, and a proximal fixed portion fixed to the catheter shaft, which are aligned from a distal end in a mentioned order, and the first radiopaque marker is disposed proximal to the distal fixed portion. This configuration suppresses increase in outer diameter of the catheter shaft at a position corresponding to the distal fixed portion of the balloon.

Preferably, the inflated portion of the balloon includes a straight tube portion, and tapered portions provided respectively at distal and proximal ends of the straight tube portion, and the cladding absent portion has a length in the longitudinal direction larger than a length of the straight tube portion of the balloon. The cladding absent portion elongated in the longitudinal direction increases the light emitting area to enable wide irradiation at a time.

Preferably, the catheter shaft includes a first lumen communicating with an inside of the balloon, and a second lumen allowing the light guiding tool to be inserted through the second lumen. The first lumen can serve as a flow path for the pressure fluid used to expand and contract the balloon, and the second lumen can serve as an insertion path for the light guiding tool.

Preferably, the cladding absent portion has a distal end positionally matching the distal end of the core. This configuration does not need a complicated step of forming the cladding absent portion while leaving the cladding in a portion including the distal end of the optical fiber, to facilitate a step of forming the light emitting area of the optical fiber.

Advantageous Effects of the Invention

The first radiopaque marker can specify a position of the catheter shaft during X-ray fluoroscopy, so that the balloon disposed at the catheter shaft can positionally match an irradiation target tissue. Since the balloon is disposed at catheter shaft, the balloon being expanded is in contact with an irradiation target tissue so that the catheter shaft can be fixed in the body. The second radiopaque marker is disposed distal to the distal end of the core, to prevent deformation and damage of the core due to stress generated upon attachment of the second radiopaque marker to the tubular member as well as to facilitate positional specification of the cladding absent portion 14 serving as the light emitting area of the optical fiber during X-ray fluoroscopy. Checking a positional relation between the first radiopaque marker and the second radiopaque marker facilitates positioning the light emitting area at the irradiation target tissue and also reduces a work burden of an operator.

BRIEF DESCRIPTION OF THE DRAWINGS

FIG. 1 is a sectional view (partially plan view) of a distal portion of a light irradiating medical device according to an embodiment of the present invention.

FIG. 2 is a sectional view of the distal portion including a balloon, of the light irradiating medical device depicted in FIG. 1.

FIG. 3 is a sectional view of a catheter shaft included in the light irradiating medical device depicted in FIG. 2.

FIG. 4 is a sectional view according to a modification example, of the light irradiating medical device depicted in FIG. 2.

FIG. 5 is a sectional view (partially plan view) according to a modification example, of the light irradiating medical device depicted in FIG. 4.

FIG. 6 is a sectional view (partially plan view) according to another modification example, of the light irradiating medical device depicted in FIG. 4.

FIG. 7 is a sectional view (partially plan view) according to still another modification example, of the light irradiating medical device depicted in FIG. 4.

FIG. 8 is an explanatory schematic view depicting a positional relation in a longitudinal direction between the first radiopaque marker and the second radiopaque marker.

FIG. 9 is an explanatory schematic view depicting a positional relation in a longitudinal direction between the first radiopaque marker and the second radiopaque marker.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

A light irradiating medical device will be described in terms of its basic configuration with reference to FIGS. 1 to 3. FIG. 1 is a sectional view (partially plan view) of a distal portion of a light irradiating medical device according to an embodiment of the present invention, FIG. 2 is a sectional view of the distal portion including a balloon, of the light irradiating medical device depicted in FIG. 1, and FIG. 3 is a sectional view of a catheter shaft included in the light irradiating medical device depicted in FIG. 2.

The light irradiating medical device according to the present invention is used in PDT and optical ablation to irradiate a treated portion as a target tissue such as a cancer cell with light having a specific wavelength in an endolumen such as a blood vessel or a gastrointestinal tract. The light irradiating medical device may be configured to be solely delivered to the treated portion or may be configured to be used along with a delivery catheter or an endoscope. Treatment with use of an endoscope involves disposing the light irradiating medical device in a body from a distal portion of a forceps port of the endoscope through the forceps port of the endoscope and delivering the light irradiating medical device to the treated portion. A light irradiating medical device 1 includes a catheter shaft 2, a balloon 5, a light guiding tool 10, a first radiopaque marker 21, and a second radiopaque marker 22.

In the present invention, the proximal side of the light irradiating medical device 1 refers to a side in a direction toward a user's hand side, that is, an operator's hand side with respect to the direction in which the catheter shaft 2 extends, and the distal side refers to a side in a direction opposite to the proximal side, that is, the direction toward a treated object. In addition, a direction from the proximal side to the distal side or a direction from the distal side to the proximal side of the catheter shaft 2 is referred to as a longitudinal direction. An inner side of the light irradiating medical device 1 refers to a direction toward a long axis center of the catheter shaft 2 in a radial direction of the catheter shaft 2, while an outer side refers to a radiation direction opposite to the inner side, Each of the catheter shaft 2, the balloon 5, the light guiding tool 10, the first radiopaque marker 21, and the second radiopaque marker 22 constituting the light irradiating medical device 1 is desired to be made of a material having biocompatibility.

The catheter shaft 2 extends in a longitudinal direction, the balloon 5 is disposed at a distal portion of the catheter shaft 2. The catheter shaft 2 has a tubular structure to have a lumen provided with the light guiding tool 10. The catheter shaft 2 is configured to be inserted to a body and is accordingly preferred to have flexuousness. Though not depicted, the catheter shaft 2 may optionally have a hub disposed at a proximal portion of the catheter shaft 2. The balloon 5 is configured to be supplied with pressure fluid from the hub through the catheter shaft 2. The balloon 5 supplied with the pressure fluid is expandable. When the pressure fluid is extracted from the balloon 5, the balloon 5 can be contracted. The balloon 5 being expanded has an outer surface in contact with an inner wall of a blood vessel, a gastrointestinal tract, or the like, so that the catheter shaft 2 can be fixed in the body.

The catheter shaft 2 may include a first lumen communicating with the inside of the balloon 5 and a second lumen allowing the light guiding tool 10 to be inserted through the second lumen. The first lumen can serve as a flow path for the pressure fluid used to expand and contract the balloon 5, and the second lumen can serve as an insertion path for the light guiding tool 10. As exemplarily depicted in FIG. 3, the catheter shaft 2 may include an inner tube 3 and an outer tube 4, the inner tube 3 and the outer tube 4 may interpose a space serving as a first lumen 2a, and the inner tube 3 has a lumen that may serve as a second lumen 2b.

The catheter shaft 2 is may be made of a synthetic resin such as a polyolefin resin (e.g. polyethylene or polypropylene), a polyamide resin (e.g. nylon), a polyester resin (e.g. PET), an aromatic polyether ketone resin (e.g. PEEK), a polyether polyamide resin, a polyurethane resin, a polyimide resin and a fluororesin (e.g. PTFE, PFA, ETFE), or a metal such as a stainless steel, a carbon steel, and a Ni—Ti alloy. These may be used alone, or two or more of them may be used in combination.

The balloon 5 may include a distal fixed portion 6 fixed to the catheter shaft 2, an inflated portion 7 not fixed to the catheter shaft 2, and a proximal fixed portion 8 fixed to the catheter shaft 2, which are aligned from a distal end in the mentioned order. In this case, preferably, the catheter shaft 2 includes the inner tube 3 and the outer tube 4, and the inner tube 3 in a distal portion of the catheter shaft 2 extends from a distal end of the outer tube 4 and penetrates the balloon 5 in the longitudinal direction. The catheter shaft 2 and the balloon 5 thus configured enable the balloon 5 to be joined to the catheter shaft 2.

The inflated portion 7 of the balloon 5 may include a straight tube portion 7a and tapered portions 7b provided respectively at distal and proximal ends of the straight tube portion 7a. When an outer surface of the straight tube portion 7a of the balloon 5 is brought into contact with the inner wall of the blood vessel, the gastrointestinal tract, or the like, the catheter shaft 2 can be fixed in the body.

The balloon 5 is preferably made of a resin. Examples of the resin constituting the balloon 5 include polyamide-based resin, polyester-based resin, polyurethane-based resin, polyolefin-based resin, vinyl chloride-based resin, silicone-based resin, and natural rubber. These may be used alone, or two or more of them may be used in combination. Among them, polyamide-based resin, polyester-based resin, and polyurethane-based resin are preferably used. An elastomer resin is preferably used for these resins from the viewpoint of flexibility and reduction in thickness of the balloon 5.

The catheter shaft 2 and the balloon 5 are each preferred to contain a light transparent material. Each of the balloon 5 and a portion of the catheter shaft 2 covered with the balloon 5 is more preferred to be made of the light transparent material. In this case, the target tissue can be efficiently irradiated with light at a position corresponding to the balloon 5 when the balloon 5 accommodates a cladding absent portion 14. Examples of the light transparent material include a synthetic resin such as a (meth)acrylic resin (e.g. polymethyl methacrylate (PMMA)), a polycarbonate resin (e.g. polydiethylene glycol bisallyl carbonate (PC)), a polystyrene resin (e.g. methyl methacrylate styrene copolymer resin (MS) or acrylonitrile-styrene resin (SAN)), a polyamide resin (e.g. nylon), or a polyolefin resin.

The catheter shaft 2 and the balloon 5 are each preferred to contain a light diffusible material, and each of the balloon 5 and the portion of the catheter shaft 2 covered with the balloon 5 is more preferred to be made of the light diffusible material. These members having light diffusibility allow the target tissue to be evenly irradiated with light. Examples of the light diffusible material include inorganic particles of titanium oxide, barium sulfate, calcium carbonate, and the like, and organic particles such as crosslinked acrylic particles and crosslinked styrene particles.

The light guiding tool 10 is disposed in the lumen of the catheter shaft 2 and is movable in the longitudinal direction. The light guiding tool 10 includes an optical fiber 11 extending in the longitudinal direction, and a tubular member 15 covering the optical fiber 11 and having light transparency. The tubular member 15 may further have light diffusibility for even light irradiation. The optical fiber 11 includes a core 12 and a cladding 13 covering the outside of the core 12, and the optical fiber 11 includes a cladding absent portion 14 disposed at a part of a distal portion of the core 12.

The light guiding tool 10 is movable in the longitudinal direction relatively to the catheter shaft 2, so that the catheter shaft 2 allows a guide wire used for delivery of the catheter shaft 2 to the target tissue to be inserted through the lumen before the light guiding tool 10 is inserted through the lumen of the catheter shaft 2.

Though not depicted, the light irradiating medical device 1 may include a guide wire extending in the longitudinal direction. In this case, the second lumen 2b can serve as an insertion path for the guide wire. The catheter shaft 2 may alternatively include a third lumen allowing the guide wire to be inserted through the third lumen.

The optical fiber 11 is a transmission path used for transmission of an optical signal to the target tissue. The optical fiber 11 has a proximal side connected to a light source such as a semiconductor laser. Neither the core 12 nor the cladding 13 is particularly limited in terms of its material, and examples of the material include plastic and glass such as quartz glass or fluoride glass.

The tubular member 15 extends in the longitudinal direction and has a tubular shape. The tubular member 15 is preferred to cover the entirety in the longitudinal direction of the optical fiber 11 so as to protect the optical fiber 11. The tubular member 15 is preferred to cover the entirety in a circumferential direction of the optical fiber 11 for a similar reason. Furthermore, the tubular member 15 has a distal end that is preferred to be disposed distal to a distal end of the optical fiber 11. This configuration prevents deformation and damage at a distal end portion of the optical fiber 11.

The tubular member 15 has only to have light transparency, and is preferred to be made of a resin. Examples of the resin contained in the tubular member 15 include a polyamide resin, a polyester resin, a polyurethane resin, a polyolefin resin, a fluororesin, a vinyl chloride resin, a silicone resin, and natural rubber. The tubular member 15 may contain only one of these resins, or two or more of these resins. Among these resins, a polyamide resin, a polyester resin, a polyurethane resin, a polyolefin resin, and a fluororesin are preferred to be contained in the tubular member 15.

The resin contained in the tubular member 15 can have, as an additive, a light diffusible material such as inorganic particles of titanium oxide, barium sulfate, calcium carbonate, or the like, or organic particles like crosslinked acrylic particles or crosslinked styrene particles.

The cladding absent portion 14 corresponds to a portion not provided with the cladding 13 and at least partially occupying a portion in the circumferential direction of the core 12, and serves as a light emitting area of the optical fiber 11. Provision of the cladding absent portion 14 thus configured achieves the light irradiating medical device of a side face irradiation type. Light emission with the balloon 5 being expanded enables the target tissue to be irradiated with light from a constant radial distance.

The cladding absent portion 14 is preferred to have no cladding 13 in the entirety in the circumferential direction of the core 12. This configuration achieves the light irradiating medical device of the side face irradiation type configured to irradiate the entirety in the circumferential direction with light from the core 12.

The cladding absent portion 14 is not particularly limited in terms of its position in the longitudinal direction as far as the cladding absent portion 14 is positioned at a part of the distal portion of the core 12, and is preferred to be provided at a portion including a distal end 12a of the core 12. This configuration facilitates provision of the cladding absent portion 14 and improves flexibility at a distal end portion of the light guiding tool 10.

As depicted in FIG. 2, the cladding absent portion 14 has a distal end 14a preferred to positionally match the distal end 12a of the core 12. This configuration does not need a complicated step of forming the cladding absent portion 14 while leaving the cladding 13 in a portion including the distal end of the optical fiber 11, to facilitate a step of forming the light emitting area of the optical fiber 11.

Upon light irradiation with the light guiding tool 10 inserted through the lumen of the catheter shaft 2, the cladding absent portion 14 has the distal end 14a preferably disposed proximal to the distal fixed portion 6 of the balloon 5 and a proximal end 14b preferably disposed distal to the proximal fixed portion 8 of the balloon 5. More preferably, the distal end 14a of the cladding absent portion 14 is disposed distal to a center of the balloon 5 in the longitudinal direction, and the proximal end 14b of the cladding absent portion 14 is disposed proximal to the center of the balloon 5 in the longitudinal direction. The cladding absent portion 14 thus positioned achieves provision of the light emitting area at a position corresponding to the balloon 5.

Preferably, the inflated portion 7 of the balloon 5 includes the straight tube portion 7a and the tapered portions 7b provided respectively at the distal and proximal ends of the straight tube portion 7a, and the cladding absent portion 14 has a length in the longitudinal direction larger than a length of the straight tube portion 7a of the balloon 5. The cladding absent portion 14 elongated in the longitudinal direction increases the light emitting area to enable wide irradiation at a time.

The length of the cladding absent portion 14 in the longitudinal direction may be equal to or less than the length of the straight tube portion 7a of the balloon 5, but is preferred to be larger than a length of the tapered portions 7b of the balloon 5 to enable wide irradiation at a time.

The cladding absent portion 14 can be formed through peeling the cladding 13 by etching, polishing, or the like. The cladding absent portion 14 is more preferred to have a coarse outer surface obtained by filing or the like. This improves light diffusibility.

The cladding absent portion 14 is preferred to be covered with the tubular member 15, and is more preferred to have the entirety in the longitudinal direction covered with the tubular member 15. This configuration protects a portion of the core 12 corresponding to the cladding absent portion 14, to suppress damage, deformation, and breaking of the core 12 at a position corresponding to the cladding absent portion 14.

The optical fiber 11 has the entirety in the longitudinal direction preferably covered with the tubular member 15. The optical fiber 11 covered with the tubular member 15 is entirely protected, to suppress damage, deformation, and breaking of the core 12.

The light irradiating medical device 1 further includes the first radiopaque marker 21 disposed at the distal portion of the catheter shaft 2, and the second radiopaque marker 22 disposed at the tubular member 15 at a position distal to the distal end 12a of the core 12. The first radiopaque marker 21 can specify a position of the catheter shaft 2 during X-ray fluoroscopy, so that the balloon 5 disposed at the catheter shaft 2 can positionally match an irradiation target tissue. The second radiopaque marker 22 is disposed distal to the distal end 12a of the core 12, to prevent deformation and damage of the core 12 due to stress generated upon attachment of the second radiopaque marker 22 to the tubular member as well as to facilitate positional specification of the cladding absent portion 14 serving as the light emitting area of the optical fiber 11 during X-ray fluoroscopy. Checking a positional relation between the first radiopaque marker 21 and the second radiopaque marker 22 facilitates positioning the light emitting area at the irradiation target tissue and also reduces a work burden of an operator. The first radiopaque marker 21 and the second radiopaque marker 22 may be hereinafter collectively called "radiopaque markers".

Each of the radiopaque markers is not particularly limited in terms of its shape, and may have a ring shape or a bar shape. The radiopaque marker may alternatively have a coil shape, or a ring shape with a slit to have a C sectional shape. The radiopaque marker having the ring shape or the coil shape is easily attached to the outside of the catheter shaft 2 or the tubular member 15. The radiopaque marker having the bar shape or the coil shape is easily disposed in the lumen of the catheter shaft 2 or the tubular member 15.

The first radiopaque marker 21 is preferred to have the ring shape and be attached to the outside of the catheter shaft 2. Similarly, the second radiopaque marker 22 is preferred to have the ring shape and be attached to the outside of the tubular member 15. These configurations facilitate attachment of the radiopaque markers.

Each of the radiopaque markers has a length in the longitudinal direction preferably smaller than the length in the longitudinal direction of the tapered portions 7b of the balloon 5. The radiopaque markers thus set in length secure a length of the light emitting area and facilitate visual recognition of the markers during X-ray fluoroscopy.

Each of the first radiopaque marker 21 and the second radiopaque marker 22 is preferred to be made of a material containing a metal material such as platinum, gold, silver, tungsten, tantalum, iridium, palladium, or an alloy of any of these metals. The radiopaque markers may be a metal marker made of the metal material, or may be a resin marker containing the metal material.

The first radiopaque marker 21 is preferred to be attached to the outside of the catheter shaft 2. This configuration prevents decrease in inner diameter of the catheter shaft 2, as well as facilitates insertion of the light guiding tool 10 to the lumen of the catheter shaft 2.

Preferably, the first radiopaque marker 21 has the ring shape and is attached to the outside of the catheter shaft 2, and the catheter shaft 2 has a portion with the first radiopaque marker 21 and the portion has an outer diameter smaller than an outer diameter of a portion without the first radiopaque marker 21. In this case, the first radiopaque marker 21 can be attached to be buried in an outer surface of the catheter shaft 2, to suppress increase in outer diameter of the catheter shaft 2 at the portion with the first radiopaque marker 21.

Preferably, the balloon 5 includes the distal fixed portion 6 fixed to the catheter shaft 2, the inflated portion 7 not fixed to the catheter shaft 2, and the proximal fixed portion 8 fixed to the catheter shaft 2, which are aligned from the distal end in the mentioned order, and the first radiopaque marker 21 is disposed proximal to the distal fixed portion 6. The first radiopaque marker 21 thus disposed suppresses increase in outer diameter of the catheter shaft 2 at a position corresponding to the distal fixed portion 6 of the balloon 5.

In the longitudinal direction, the first radiopaque marker 21 is preferred to be positioned correspondingly to the inflated portion 7 of the balloon 5, and is more preferred to be positioned correspondingly to the straight tube portion 7a or one of the tapered portions 7b of the inflated portion 7.

The first radiopaque marker 21 may alternatively be positioned correspondingly to a portion including a boundary between the straight tube portion 7a and one of the tapered portions 7b. The first radiopaque marker 21 may still alternatively be positioned correspondingly to at least one of a distal end portion and a proximal end portion of the straight tube portion 7a. The first radiopaque marker 21 thus disposed further facilitates positional checking of the catheter shaft 2 during X-ray fluoroscopy.

Assume that a center 7c of the inflated portion 7 of the balloon 5 and a center 14c of the cladding absent portion 14 are matched in the longitudinal direction. In this case, the first radiopaque marker 21 has a proximal end preferably disposed distal to the distal end 14a of the cladding absent portion 14. The first radiopaque marker 21 thus disposed to be away from the light emitting area (the cladding absent portion 14) prevents heat generation of the first radiopaque marker 21 due to light energy upon light irradiation.

The second radiopaque marker 22 has a proximal end preferably disposed distal to the distal end 14a of the cladding absent portion 14, and more preferably disposed distal to the distal end 14a of the cladding absent portion 14 at least by a length of the first radiopaque marker 21 in the longitudinal direction. The second radiopaque marker 22 thus disposed to be away from the light emitting area prevents heat generation of the second radiopaque marker 22 due to light energy. Furthermore, the first radiopaque marker 21 and the second radiopaque marker 22 are more distinguishable from each other even during X-ray fluoroscopy.

Assume that the center 7c of the inflated portion 7 of the balloon 5 and the center 14c of the cladding absent portion 14 are matched in the longitudinal direction. In this case, as depicted in FIG. 2, the second radiopaque marker 22 has a distal end preferably disposed proximal to a distal end of the distal fixed portion 6 of the balloon 5, and the second radiopaque marker 22 has the proximal end preferably disposed distal to the center of the balloon 5 in the longitudinal direction. This disposition secures the length of the light emitting area as well as facilitates visual recognition of the marker.

The second radiopaque marker 22 is preferred to be longer in the longitudinal direction than the first radiopaque marker 21. The second radiopaque marker 22 is not completely hidden behind the first radiopaque marker 21 even in a case where the two markers are overlapped with each other. This configuration facilitates visual recognition of the positions of the markers as well as positional specification of the optical fiber 11.

Preferably, the second radiopaque marker 22 has the ring shape and is attached to the outside of the tubular member 15, and the tubular member 15 has a portion with the second radiopaque marker 22 and the portion has an outer diameter smaller than an outer diameter of a portion of the tubular member 15 without the second radiopaque marker 22. In this case, the second radiopaque marker 22 can be attached to be buried in an outer surface of the tubular member 15, to suppress increase in outer diameter of the tubular member 15 at the portion with the second radiopaque marker 22. Furthermore, this configuration enables treatment of a deep tissue or an endoluminal tissue having a small inner diameter, which has not been reached so far. Examples of a method of attaching the marker in this manner include caulking the second radiopaque marker 22 at a desired position of the tubular member 15. The second radiopaque marker 22 is preferred to be made of a metal in order to be caulked to the outside of the catheter shaft 2 or the tubular member 15.

In the case where the second radiopaque marker 22 has the ring shape and is attached to the outside of the tubular member 15, the second radiopaque marker 22 is preferred to be thinner than the tubular member 15. The second radiopaque marker 22 and the tubular member 15 are set in thickness in this manner, to secure flexibility of the portion of the tubular member 15 provided with the second radiopaque marker 22.

The tubular member 15 has an inner diameter preferably constant in size in the longitudinal direction so as to allow the optical fiber 11 to be easily inserted to the lumen of the tubular member 15.

The outer diameter of the tubular member 15 is preferred to be set to cause the light guiding tool 10 to be easily movable in the longitudinal direction in the lumen of the catheter shaft 2. For example, the outer diameter of the tubular member 15 may gradually decrease toward the distal end, or may be constant in size in the longitudinal direction.

Preferably, the first radiopaque marker 21 has the ring shape and is attached to the outside of the catheter shaft 2, and the second radiopaque marker 22 has the length in the longitudinal direction larger than the length in the longitudinal direction of the first radiopaque marker 21. The second radiopaque marker 22 is not completely hidden behind the first radiopaque marker 21 even in the case where the two markers are overlapped with each other. This configuration facilitates positional specification of the light emitting area of the optical fiber 11.

FIG. 4 is a sectional view according to a modification example, of the light irradiating medical device 1 depicted in FIG. 2. The tubular member 15 has a distal end portion having an opening that may be sealed as depicted in FIG. 4. This configuration inhibits the optical fiber 11 disposed in the lumen of the tubular member 15 from falling from a distal end surface of the light guiding tool 10. The opening at the distal end portion of the tubular member 15 is sealed by bringing a heat generator such as a heater or a soldering iron close to the distal end portion of the tubular member 15 and welding the distal end portion of the tubular member 15, enclosing an adhesive resin from the distal end portion of the tubular member 15, or the like.

In a case where the opening at the distal end portion of the tubular member 15 is sealed to dispose a distal end of the lumen of the tubular member 15 proximal to a distal end 15a of the tubular member 15 as depicted in FIG. 4, the proximal end of the second radiopaque marker 22 is preferred to be disposed distal to the distal end of the lumen of the tubular member 15. This disposition prevents deformation and damage of the optical fiber 11 when the second radiopaque marker 22 is attached to the tubular member 15.

The exemplary case where the second radiopaque marker 22 is attached to the outside of the tubular member 15 has been described above with reference to FIGS. 1 to 4. Described next with reference to FIGS. 5 to 7 is another exemplary case where the second radiopaque marker 22 is disposed in the lumen of the tubular member 15. FIGS. 5 to 7 each are a sectional view (partially plan view) according to a modification example, of the light irradiating medical device 1 depicted in FIG. 4. As depicted in FIGS. 5 to 7, the second radiopaque marker 22 is preferred to be disposed in the lumen of the tubular member 15 at a position distal to the distal end 12a of the core 12. The second radiopaque marker 22 has an outer diameter smaller than the inner diameter of the tubular member 15 in this case. Even if the second radiopaque marker 22 is provided in the tubular member 15, the light guiding tool 10 can be decreased in diameter at the position distal to the distal end 12a of the core 12 in this configuration.

The distal end 15a of the tubular member 15 is preferred to be positioned distal to the distal end 12a of the core 12. In this case, the distal end of the lumen of the tubular member 15 is preferred to be disposed distal to the distal end 12a of the core 12. The second radiopaque marker 22 can thus be disposed in the lumen of the tubular member 15 (specifically, a portion, from the distal end of the lumen of the tubular member 15 to the distal end 12a of the core 12, of the lumen of the tubular member 15).

As depicted in FIG. 5, the second radiopaque marker 22 may have the coil shape. Particularly, the second radiopaque marker 22 is preferred to have the coil shape at least in a distal portion, and is more preferred to have the coil shape in the entirety in the longitudinal direction. The second radiopaque marker 22 having the coil shape in this manner causes the light guiding tool 10 to be more deformable at a position distal to the distal end 12a of the core 12 so as to follow a shape of the endolumen.

As depicted in FIG. 6, the second radiopaque marker 22 may have the bar shape. This shape simplifies a step of forming the second radiopaque marker 22. The second radiopaque marker 22 may have a solid bar shape or a hollow bar shape. The second radiopaque marker 22 has a section that is perpendicular to the longitudinal direction and can have a circular shape, an elliptical shape, a polygonal shape, or any combination of these shapes. The section of the second radiopaque marker 22 is preferred to have the circular shape or the elliptical shape in order to protect an inner wall of the tubular member 15.

In the case where the second radiopaque marker 22 is disposed in the lumen of the tubular member 15, the outer diameter of the second radiopaque marker 22 is preferred to be smaller than an outer diameter of the core 12 at the cladding absent portion 14. The outer diameter of the marker is set in this manner to enhance flexibility at a distal portion of the light guiding tool 10.

In the case where the second radiopaque marker 22 has the ring shape or the coil shape and is disposed in the lumen of the tubular member 15, the outer diameter of the core 12 at the cladding absent portion 14 is preferred to be larger than an inner diameter of the second radiopaque marker 22. This configuration prevents the cladding absent portion 14 from entering the second radiopaque marker 22.

Assume that the center 7c of the inflated portion 7 of the balloon 5 and the center 14c of the cladding absent portion 14 are matched in the longitudinal direction. In this case, as depicted in FIGS. 5 to 7, the second radiopaque marker 22 has the distal end preferably disposed distal to the distal end of the distal fixed portion 6 of the balloon 5, and the second radiopaque marker 22 has the proximal end preferably disposed distal to the center of the balloon 5 in the longitudinal direction. This disposition secures the lengths of the light emitting area and the marker.

In the case where the second radiopaque marker 22 is disposed in the lumen of the tubular member 15, the second radiopaque marker 22 and the cladding absent portion 14 interpose a spacer, though not depicted. The spacer thus provided causes no direct contact between the cladding absent portion 14 and the second radiopaque marker 22, to prevent damage of the core 12. Examples of the spacer include a cover member covering a distal end surface of the cladding absent portion 14. The spacer may contain a light reflective material. The spacer thus reflects irradiation light from the distal end 12a of the core 12 to increase quantity of irradiation light from the cladding absent portion 14. Examples of the light reflective material include aluminum, gold, silver, copper, tin, titanium dioxide, tantalum pentoxide, aluminum oxide, silicon dioxide, magnesium fluoride, or any combination of these materials.

The distal end portion of the tubular member 15 may be provided with a resin chip 16 as depicted in FIG. 7. This configuration inhibits the second radiopaque marker 22 disposed in the lumen of the tubular member 15 from falling from the distal end surface of the light guiding tool 10. The resin chip 16 can be formed into a hemispherical shape, a semiellipse spherical shape, a columnar shape, a polygonal prism shape, or the like. The resin chip 16 is preferred to be partially disposed in the lumen of the tubular member 15. Furthermore, the resin chip 16 is preferred to have a cork shape and be inserted to the lumen of the tubular member 15. The resin chip 16 can be made of a material similar to the material for the tubular member 15.

In a case where the catheter shaft 2 and the light guiding tool 10 have a relative positional relation adjusted to match the center 7c of the inflated portion 7 of the balloon 5 and the center 14c of the cladding absent portion 14 in the longitudinal direction, the first radiopaque marker 21 and the second radiopaque marker 22 have only to be disposed to enable recognition that the markers are disposed at positions corresponding to each other, and are not particularly limited in terms of their relative positional relation. When positional adjustment is executed to match the center 7c of the inflated portion 7 of the balloon 5 and the center 14c of the cladding absent portion 14 in the longitudinal direction as exemplarily depicted in FIGS. 1, 2, and 4, the proximal end of the second radiopaque marker 22 may be disposed distal to a distal end of the first radiopaque marker 21. Though not depicted, the distal end of the second radiopaque marker 22 may be disposed proximal to the proximal end of the first radiopaque marker 21. The markers can thus be displaced from each other in the longitudinal direction, to suppress locally enhanced rigidity at a distal end portion of the light irradiating medical device 1. The two markers are observed to be spaced apart from each other during X-ray fluoroscopy.

When positional adjustment is executed to match the center 7c of the inflated portion 7 of the balloon 5 and the center 14c of the cladding absent portion 14 in the longitudinal direction as depicted in FIGS. 5 to 7, the distal end of the second radiopaque marker 22 may be disposed distal to the distal end of the first radiopaque marker 21, and the proximal end of the second radiopaque marker 22 may be disposed proximal to the proximal end of the first radiopaque marker 21. The markers are observed to have a cross shape during X-ray fluoroscopy, to facilitate visual recognition of the positions of the markers.

FIGS. 8 and 9 are explanatory schematic views each depicting a positional relation in the longitudinal direction between the first radiopaque marker 21 and the second radiopaque marker 22. FIGS. 8 and 9 each have a left end corresponding to a distal end and a right end corresponding to a proximal end. When positional adjustment is executed to match the center 7c of the inflated portion 7 of the balloon 5 and the center 14c of the cladding absent portion 14 in the longitudinal direction as depicted in FIG. 8, the proximal end of the second radiopaque marker 22 may be disposed proximal to the distal end of the first radiopaque marker 21 as well as distal to the proximal end of the first radiopaque marker 21, and the distal end of the second radiopaque marker 22 may be disposed distal to the distal end of the first radiopaque marker 21. When positional adjustment is executed to match the center 7c of the inflated portion 7 of the balloon 5 and the center 14c of the cladding absent portion 14 in the longitudinal direction as depicted in FIG. 9, the distal end of the second radiopaque marker 22 may be disposed proximal to the distal end of the first radiopaque marker 21 as well as distal to the proximal end of the first radiopaque marker 21, and the proximal end of the second radiopaque marker 22 may be disposed proximal to the proximal end of the first radiopaque marker 21. The markers are observed to have a T shape during X-ray fluoroscopy, to facilitate visual recognition of the positions of the markers.

There may be provided still another radiopaque marker for easier positional checking of the tubular member 15 or the catheter shaft 2. As depicted in FIGS. 1, 2, and 4 to 7, the light irradiating medical device 1 is preferred to further include a third radiopaque marker 23 disposed at the tubular member 15 at a position proximal to the proximal end 14b of the cladding absent portion 14. The radiopaque markers are thus disposed at respective ends of the cladding absent portion 14 serving as the light emitting area in the longitudinal direction of the tubular member 15, to further facilitate positional specification of the light emitting area during X-ray fluoroscopy.

As depicted in FIGS. 1 to 7, the light irradiating medical device 1 is preferred to further include a fourth radiopaque marker 24 disposed at the catheter shaft 2 at a position proximal to the first radiopaque marker 21. This configuration further facilitates positional specification of the catheter shaft 2 in the longitudinal direction during X-ray fluoroscopy.

Each of the third radiopaque marker 23 and the fourth radiopaque marker 24 is not particularly limited in terms of its shape, and can have a ring shape or a coil shape.

The third radiopaque marker 23 is preferred to have the ring shape and be attached to the outside of the tubular member 15.

The third radiopaque marker 23 has an outer diameter smaller than the inner diameter of the catheter shaft 2 (a diameter of the second lumen 2b in FIG. 3) so as to cause the light guiding tool 10 to be disposed in the lumen of the catheter shaft 2.

In a case where each of the second radiopaque marker 22 and the third radiopaque marker 23 has the ring shape and is attached to the outside of the tubular member 15, the outer diameter of the tubular member 15 at the portion with the second radiopaque marker 22 is preferred to be smaller than an outer diameter of the tubular member 15 at a portion with the third radiopaque marker 23. Increase in outer diameter of the tubular member 15 can be suppressed at the portion with the second radiopaque marker 22, and the tubular member 15 can thus easily secure flexibility to easily follow the shape of the endolumen. At the portion with the third radiopaque marker 23, the tubular member 15 can prevent the optical fiber 11 from being excessively fastened as well as suppress damage, deformation, and breaking of the optical fiber 11.

The fourth radiopaque marker 24 is preferred to have the ring shape and be attached to the outside of the catheter shaft 2. The fourth radiopaque marker 24 can be disposed at the catheter shaft 2, similarly to the first radiopaque marker 21.

The third radiopaque marker 23 is preferred to be longer in the longitudinal direction than the fourth radiopaque marker 24. When the markers are set in length in the longitudinal direction in this manner, the third radiopaque marker 23 is not completely hidden behind the fourth radiopaque marker 24 even if the two markers are overlapped with each other. This configuration facilitates visual recognition of the positions of the markers as well as positional specification of the light emitting area of the optical fiber 11.

In the case where the catheter shaft 2 and the light guiding tool 10 have the relative positional relation adjusted to match the center 7c of the inflated portion 7 of the balloon 5 and the center 14c of the cladding absent portion 14 in the longitudinal direction, the third radiopaque marker 23 and the fourth radiopaque marker 24 have only to be disposed to enable recognition that the markers are disposed at positions corresponding to each other, and are not particularly limited in terms of their relative positional relation. When positional adjustment is executed to match the center 7c of the inflated portion 7 of the balloon 5 and the center 14c of the cladding absent portion 14 in the longitudinal direction as exemplarily depicted in FIGS. 1, 2, and 4 to 7, the fourth radiopaque marker 24 has a proximal end that may be disposed distal to a distal end of the third radiopaque marker 23. Though not depicted, the fourth radiopaque marker 24 has a distal end that may be disposed proximal to a proximal end of the third radiopaque marker 23. The markers can thus be displaced from each other in the longitudinal direction, to suppress locally enhanced rigidity. The two markers are observed to be spaced apart from each other during X-ray fluoroscopy.

Though not depicted, when positional adjustment is executed to match the center 7c of the inflated portion 7 of the balloon 5 and the center 14c of the cladding absent portion 14 in the longitudinal direction, the distal end of the fourth radiopaque marker 24 may be disposed distal to the distal end of the third radiopaque marker 23, and the proximal end of the fourth radiopaque marker 24 may be disposed proximal to the proximal end of the third radiopaque marker 23. The markers are observed to have a cross shape during X-ray fluoroscopy, to facilitate visual recognition of the positions of the markers.

Though not depicted, when positional adjustment is executed to match the center 7c of the inflated portion 7 of the balloon 5 and the center 14c of the cladding absent portion 14 in the longitudinal direction, the proximal end of the fourth radiopaque marker 24 may be disposed proximal to the distal end of the third radiopaque marker 23 as well as proximal to the proximal end of the third radiopaque marker 23, and the distal end of the fourth radiopaque marker 24 may be disposed distal to the distal end of the third radiopaque marker 23. According to a different aspect, when positional adjustment is executed to match the center 7c of the inflated portion 7 of the balloon 5 and the center 14c of the cladding absent portion 14 in the longitudinal direction, the proximal end of the fourth radiopaque marker 24 may be disposed proximal to the proximal end of the third radiopaque marker 23, and the distal end of the fourth radiopaque marker 24 may be disposed proximal to the distal end of the third radiopaque marker 23 as well as distal to the proximal end of the third radiopaque marker 23. The markers are observed to have a T shape during X-ray fluoroscopy, to facilitate visual recognition of the positions of the markers.

The third radiopaque marker 23 is preferred to be longer in the longitudinal direction than the fourth radiopaque marker 24. When the markers are set in length in the longitudinal direction in this manner, the third radiopaque marker 23 is not completely hidden behind the fourth radiopaque marker 24 even if the two markers are overlapped with each other. This configuration facilitates visual recognition of the positions of the markers as well as positional specification of the light emitting area of the optical fiber 11.

When positional adjustment is executed to match the center 7c of the inflated portion 7 of the balloon 5 and the center 14c of the cladding absent portion 14 in the longitudinal direction, the distal end of at least one of the third radiopaque marker 23 and the fourth radiopaque marker 24 is preferred to be disposed proximal to the proximal end of the cladding absent portion 14. This disposition facilitates positional specification of the proximal end of the cladding absent portion 14 serving as the light emitting area.

The first to fourth radiopaque markers can have lengths in the longitudinal direction and positional relations obtained by any appropriate combination of the above aspects.

This application claims the benefit of the priority date of Japanese patent application No. 2018-186895 filed on Oct. 1, 2018. All of the contents of the Japanese patent application No. 2018-186895 filed on Oct. 1, 2018 are incorporated by reference herein.

REFERENCE SIGNS LIST

1: Light irradiating medical device
2: Catheter shaft
2a: First lumen
2b: Second lumen
3: Inner tube
4: Outer tube
5: Balloon
6: Distal fixed portion
7: Inflated portion
7a: Straight tube portion
7b: Tapered portion
7c: Center of the inflated portion in the longitudinal direction
8: Proximal fixed portion
10: Light guiding tool
11: Optical fiber
12: Core
12a: Distal end of the core
13: Cladding
14: Cladding absent portion
14a: Distal end of the cladding absent portion
14b: Proximal end of the cladding absent portion
14c: Center of the cladding absent portion in the longitudinal direction
15: Tubular member
15a: Distal end of the tubular member
16: Resin chip
21: First radiopaque marker
22: Second radiopaque marker
23: Third radiopaque marker
24: Fourth radiopaque marker

The invention claimed is:

1. A light irradiating medical device comprising:
a catheter shaft extending from a proximal end to a distal end in a longitudinal direction;
a balloon disposed at a distal portion of the catheter shaft; and
a light guiding tool disposed in a lumen of the catheter shaft and movable in the longitudinal direction,
the light guiding tool including an optical fiber extending in the longitudinal direction and a tubular member covering the optical fiber and having light transparency,
the optical fiber including a core and a cladding covering an outside of the core, and the optical fiber including a cladding absent portion disposed at a part of a distal portion of the core,
the light irradiating medical device further comprising:

a first radiopaque marker disposed at the distal portion of the catheter shaft; and a second radiopaque marker disposed at the tubular member at a position more distal than a distal end of the core of the optical fiber.

2. The light irradiating medical device according to claim 1, wherein the second radiopaque marker has a ring shape, through which the tubular member is inserted such that the second radiopaque marker is disposed at an outside of the tubular member, and a portion of the tubular member at which the second radiopaque marker is disposed has an outer diameter smaller than an outer diameter of a portion of the tubular member at which the second radiopaque marker is not disposed.

3. The light irradiating medical device according to claim 1, wherein the second radiopaque marker is disposed in a lumen of the tubular member at a position more distal than the distal end of the core of the optical fiber.

4. The light irradiating medical device according to claim 1, wherein the first radiopaque marker has a ring shape, through which the catheter shaft is inserted such that the first radiopaque marker is disposed at an outside of the catheter shaft, and the second radiopaque marker has a length in the longitudinal direction larger than a length in the longitudinal direction of the first radiopaque marker.

5. The light irradiating medical device according to claim 1, wherein the second radiopaque marker has a coil shape.

6. The light irradiating medical device according to claim 3, wherein the second radiopaque marker has a bar shape.

7. The light irradiating medical device according to claim 1, further comprising a third radiopaque marker disposed at the tubular member at a position more proximal than a proximal end of the cladding absent portion of the optical fiber.

8. The light irradiating medical device according to claim 7, further comprising a fourth radiopaque marker disposed at the catheter shaft at a position more proximal than the first radiopaque marker.

9. The light irradiating medical device according to claim 1, wherein the balloon includes a distal fixed portion fixed to the catheter shaft, an inflating portion not fixed to the catheter shaft, and a proximal fixed portion fixed to the catheter shaft, which are aligned from a distal end in a mentioned order, and the first radiopaque marker is disposed more proximal than the distal fixed portion.

10. The light irradiating medical device according to claim 9, wherein the inflating portion of the balloon includes a straight tube portion, and tapered portions provided respectively at distal and proximal ends of the straight tube portion, and the cladding absent portion has a length in the longitudinal direction larger than a length of the straight tube portion of the balloon.

11. The light irradiating medical device according to claim 1, wherein the catheter shaft includes a first lumen communicating with an inside of the balloon, and a second lumen allowing the light guiding tool to be inserted through the second lumen.

12. The light irradiating medical device according to claim 1, wherein the cladding absent portion extends in the longitudinal direction to the distal end of the optical fiber such that a distal end of the cladding absent portion conforms with the distal end of the core.

13. The light irradiating medical device according to claim 1, wherein the cladding absent portion serves as a light emitting area of the optical fiber.

14. The light irradiating medical device according to claim 1, wherein the tubular member of the light guiding tool is different from the catheter shaft, and the tubular member of the light guiding tool is disposed in the lumen of the catheter shaft.

\* \* \* \* \*